United States Patent
Fenner et al.

(10) Patent No.: US 6,501,356 B2
(45) Date of Patent: Dec. 31, 2002

(54) METHOD FOR DETERMINING THE REMAINING SERVICE LIFE OF THE SWITCH CONTACTS IN AN ELECTRIC SWITCHING DEVICE AND ELECTRIC SWITCHING DEVICE WITH AN EVALUATION UNIT FOR CARRYING OUT SAID METHOD

(75) Inventors: Matthias Fenner, Wiesbaden (DE); Frank Berger, Swisttal-Miel (DE); Klaus-Jochen Froehlich, Dresden (DE); Eckhardt Pridoehl, Dresden (DE)

(73) Assignee: Moeller GmbH, Bonn (DE)

( * ) Notice: Subject to any disclaimer, the term of this patent is extended or adjusted under 35 U.S.C. 154(b) by 0 days.

(21) Appl. No.: 10/102,191

(22) Filed: Mar. 20, 2002

(65) Prior Publication Data

US 2002/0167776 A1 Nov. 14, 2002

Related U.S. Application Data

(63) Continuation of application No. PCT/EP00/08770, filed on Sep. 8, 2000.

(30) Foreign Application Priority Data

Sep. 20, 1999 (DE) .......................... 199 45 058

(51) Int. Cl.$^7$ .......................... H01H 51/00; H01H 7/16; H01H 75/00; C21B 7/24; G01N 21/00
(52) U.S. Cl. .......................... 335/156; 73/584; 73/602; 73/627; 73/628
(58) Field of Search .......................... 335/156; 73/570, 73/584, 596, 602, 627–629, 632

(56) References Cited

U.S. PATENT DOCUMENTS

| | | | |
|---|---|---|---|
| 4,501,149 A | 2/1985 | Konno et al. | 73/587 |
| 5,798,457 A | 8/1998 | Paulson | 73/587 |
| 6,313,636 B1 * | 11/2001 | Pohl et al. | 324/421 |

FOREIGN PATENT DOCUMENTS

| | | |
|---|---|---|
| DE | 4028721 | 3/1992 |
| EP | 0333139 | 9/1989 |
| JP | 58156851 | 9/1983 |

* cited by examiner

Primary Examiner—Ramon M. Barrera
(74) Attorney, Agent, or Firm—Davidson, Davidson & Kappel, LLC

(57) ABSTRACT

A method for determining a remaining service life of switching contacts in an electric switching device. The method includes operating the switching contacts so as to produce structure-borne sound signals, capturing the structure-borne sound signals, performing a Fourier transform on the structure-borne sound signals in a plurality of discrete time windows so as to produce a sonogram, determining a plurality of function values using the sonogram, and evaluating the plurality of function values using an evaluation device. Also a electrical switching device including first and second switching contacts, a sound sensor configured to capture structure-borne sound signals produced by an operation of the first and second switching contacts, and an evaluation device configured to evaluate the first structure-borne signals so as to determine a remaining service life of the first and second switching contacts.

30 Claims, 3 Drawing Sheets

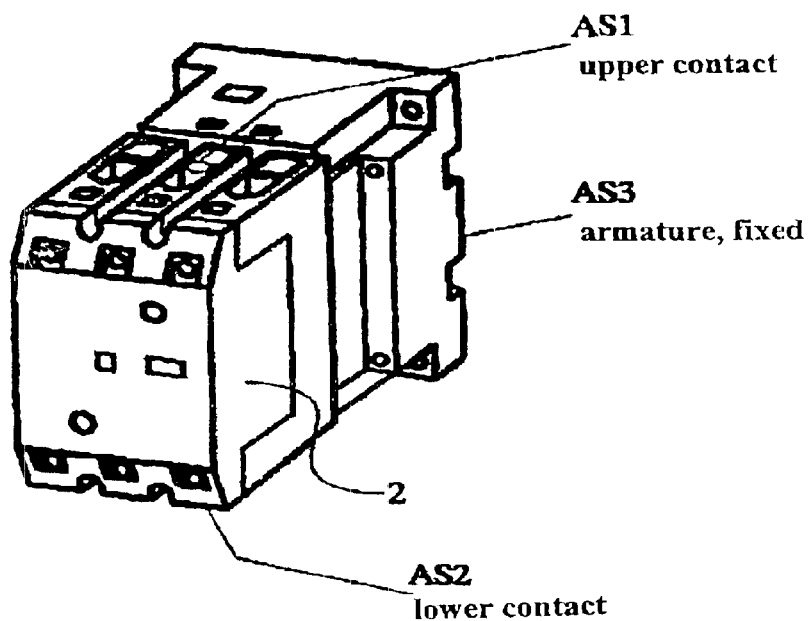
*Fig. 1*
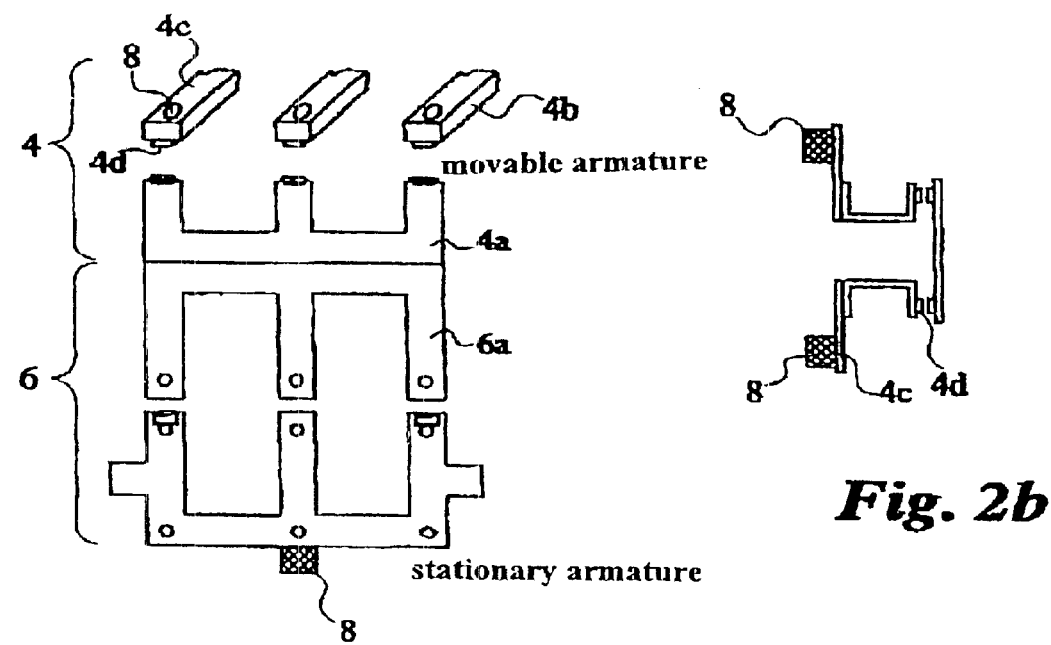
*Fig. 2a*   *Fig. 2b*

METHOD FOR DETERMINING THE REMAINING SERVICE LIFE OF THE SWITCH CONTACTS IN AN ELECTRIC SWITCHING DEVICE AND ELECTRIC SWITCHING DEVICE WITH AN EVALUATION UNIT FOR CARRYING OUT SAID METHOD

BACKGROUND INFORMATION

The present invention relates to a method for determining the remaining service life of the switching contacts in an electric switching device and to an electric switching device including an evaluation unit that can be used in determining the remaining service life of the switching contacts in the device.

German Patent Application No. DE 40 28 721 C2 describes a method for determining the remaining service life of switching devices and an arrangement for carrying out the method. According to this method, only measurable values are used which can be measured in the cables of the device. Here, the structural changes to the switching device are to be intentionally avoided.

SUMMARY OF THE INVENTION

An object of the present invention is to provide a method and a device for carrying out the method by which the characterization of switching contact states with respect to the expected service life, or with respect to the respective existing state of an electric switching contact is improved.

The present invention provides a method for determining a remaining service life of switching contacts in an electrical switching device. The method includes operating the switching contacts so as to produce structure-borne sound signals, capturing the structure-borne sound signals, performing a Fourier transform on the structure-borne sound signals in a plurality of discrete time windows so as to produce a sonogram, determining a plurality of function values using the sonogram, evaluating the plurality of function values using an evaluation device.

The invention further provides an electrical switching device the includes a first switching contact, a second switching in an operable relationship to the first switching contact, a sound sensor configured to capture structure-borne sound signals produced by an operation of the first and second switching contacts, and an evaluation device configured to evaluate the structure-borne signals so as to determine a remaining service life of at least one of the first and second switching contacts.

According to the present invention, structure-borne sound signals of the switching contact arrangement which are produced by the switching operation in the contact pieces are captured, the captured structure-borne sound signals are subjected to a Fourier transform in discrete time windows to produce a sonogram, and individual function values are selectively determined from the sonogram and evaluated using an evaluation device. Preferred function values are the peak value of at least one sonogram amplitude, the rise time of a sonogram amplitude from the occurrence of the signal to its maximum value, the decay time of the sonogram amplitude as well as the centroid of the amplitude area or of the amplitude space of a sonogram amplitude or of an amplitude space.

In a preferred embodiment, by selectively choosing three different frequency bands (frequency ranges) within which to capture and evaluate structure-borne sound signals of the contact pieces, interference effects are suppressed to the greatest possible extent (frequency ranges having high noise components are selectively masked) and meaningful signals are individually determined for each switching contact. According to the present invention, this is achieved in that an integral is formed over the signals of the structure-borne sound waves of a switching contact in at least two of three frequency bands, that in the third frequency band, either an integral of the occurring sound signals is formed as well or only the amplitude value of the sonographically determined sound signal shape (sonic response) is determined, and the values obtained in this manner from the three frequency bands are evaluated using an evaluation device. In this manner, the structure-borne sound signals occurring inside a switching contact during a switching operation (opening and/or closing operation of the switching contacts) are captured and evaluated to assess the remaining service life.

Since a contact piece has particularly characteristic properties in different frequency bands which properties change as a function of its state of wear, it is possible to make a precise statement on the wear state and the associated remaining service life of the switching contact by evaluating these properties.

The bandwidths of 20 kHz–35 kHz, 50 kHz–125 kHz and 175 kHz–225 kHz have been found to be particularly preferable frequency ranges for the three frequency bands. In this connection, within the first frequency band (20–35 kHz), the amplitude response of the sonic response is determined from an appertaining sonogram and, within the second and third frequency bands (50–125 kHz and 175–225 kHz), a formed integrated value of the structure-borne sound signal amplitudes is formed. In a different procedure, it is also possible to integrate the sound signal amplitudes in all three frequency bands, and to evaluate these values afterwards.

The determination of the function values of the sonic response determined in an appertaining sonogram is preferable performed in a time interval of three to six milliseconds after the closing of the switching contacts (or the occurrence of the first structure-borne sound signal).

The method according to the present is carried out using a switching device which features an evaluation device.

In a first embodiment, the evaluation device is integrated in the switching device in addition to with sensors for structure-borne sound. In this context, the structure-borne sound sensors are coupled to the switching contact in the form of piezoelectric elements in a manner which permits capture of sound waves arising in the switching contact or in the contact piece itself.

In a preferred embodiment, the structure-borne sound sensors are arranged on the contact piece carrier via a ceramic crystal carrier or via an element which is operationally connected to the contact piece carrier with respect to the transmission of the structure-borne sound waves. In this manner, a galvanic separation between the sound sensor and the contact piece carrier is achieved while at the same time ensuring high-quality transmission of the structure-borne sound waves.

In a second embodiment, the evaluation device is designed as a separate device or as a part of a multipurpose device (multipurpose measuring instrument or diagnostic unit). In this context, as described above, the sound sensors are arranged immediately in the switching unit itself and can be contacted from outside via an interface. Thus, the expected remaining service life of the switching contacts of a switching device according to the present invention can be determined, when necessary, via an external evaluation device.

BRIEF DESCRIPTION OF THE DRAWINGS

Further details and advantages of the present invention follow from the following exemplary embodiment which will be explained on the basis of the drawings, in which:

FIG. 1 shows a switching device according to the present invention in the form of a contactor;

FIGS. 2a, b show, in a schematic representation, the magnetic drive and the contact system of a switching device according to the present invention;

DETAILED DESCRIPTION

Figure 3:
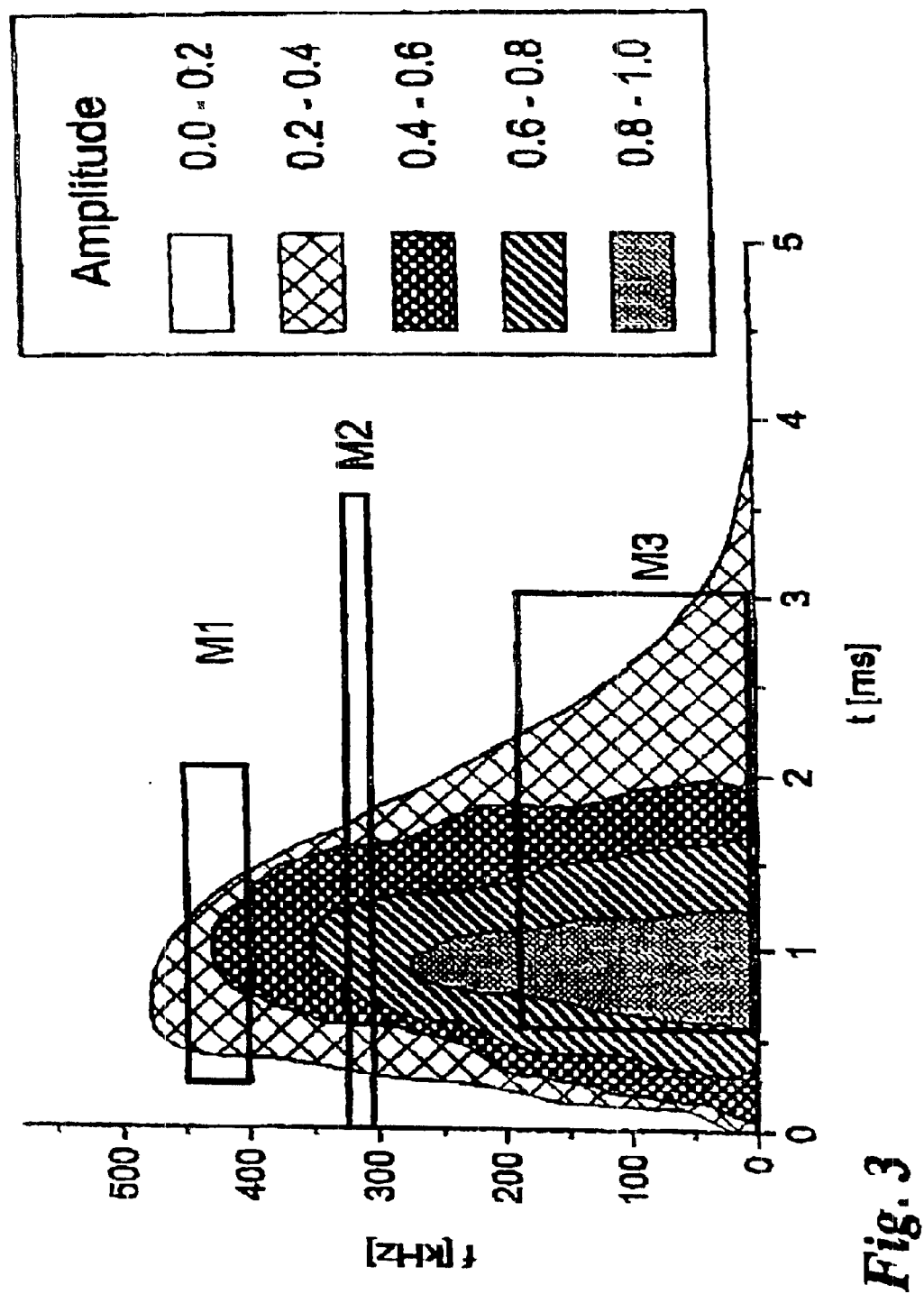
FIG. 3 is a schematic representation of a sonogram shape of a switching device according to FIGS. 1 and 2.

FIG. 1 shows a switching device according to the present invention in the form of a contactor. A contactor of that kind includes a multi-part housing 2 in which are arranged a contact system (here three-pole), a magnetic drive acting upon this contact system, as well as electronic and/or mechanical tripping elements. AS1, AS2 and AS3 indicate positions at which sound capturing means in the form of acoustic sensors (AS) can be positioned in the switching device. Preferred positions for the attachment of the structure-borne sound sensors include the positioning on contact piece 4d itself (for example, between the contact piece and the contact piece carrier), on contact piece carrier 4c (in particular, on the side diametrically opposite the contact piece), or else, on the terminals of the switching device.

FIGS. 2a and 2b show a contact system 4 with appertaining magnetic drive 6 in a schematic view. In this context, the contact system is essentially constituted by a movable switching contact 4a, here, in the form of a three-pole contact bridge which is driven via movable armature 6a of magnetic drive 6, and by stationary switching contacts 4b.

Moreover, the switching device according to the present invention has an evaluation unit, in particular, a microprocessor, for determining the remaining service life of the switching contacts.

Moreover, a switching device of that kind is designed with sound sensor 8 for capturing structure-borne sound signals. These sound sensors for capturing structure-borne sound 8 are advantageously constituted by piezoelectric elements. These are piezoelectric elements which deliver precise measuring signals over a wide range of high frequencies, preferably 20 kHz to 225 kHz or even 500 kHz.

Preferably, at least one stationary switching contact 4b is assigned at least one sound sensor for capturing structure-borne sound 8. As shown in FIG. 2b, such a sound sensor for capturing structure-borne sound can be arranged on contact carrier 4c of the associated contact piece 4d. In a particularly preferred embodiment of the present invention, the sound sensor for capturing structure-borne sound 8 which in each case is assigned to a switching contact 4a, 4b is mounted in such a manner that a galvanic separation is guaranteed. To this end, a ceramic crystal carrier is preferably mounted between contact piece carrier 4c and sound sensor for capturing structure-borne sound 8. In this manner, a reliable galvanic separation is achieved without negatively influencing the capture of sound.

In a particularly advantageous embodiment, at least two sound sensors for capturing structure-borne sound 8 are assigned to one switching contact 4a, 4b or to the respective contact piece 4d. This makes it possible for a contact piece 4d to be examined in a partial and spatially resolved manner. This is an advantage since contact pieces 4d are generally subject only to very irregular wear (erosion), and a qualitatively better determination of the condition of individual partial areas of contact piece 4d is made possible in this manner. For this embodiment, it is advantageous to arrange the individual sound sensors for capturing structure-borne sound 8 on contact piece carrier 4c itself below the associated contact piece 4d on the side opposite the contact piece 4d. Advantageously, one contact piece 4d is assigned four sound sensors 8. In this context, these are arranged, in particular, in such a manner that each sound sensor 8 covers one of four coordinate fields of a Cartesian coordinate system and that, consequently, the entire contact piece area (i.e., the complete erosion of the entire contact piece surface) is imaged by sound sensors 8 and the evaluation device.

In another embodiment, the different sound sensors 8 (here piezos) assigned to a single contact piece 4d can be concentrically nested within one another. Thus, it is possible for annular partial areas of a contact piece 4d to be evaluated in a differentiated manner. Depending on the application case, the most different other geometrical embodiments are conceivable as well.

Moreover, the present invention relates to a method for determining the remaining service life of the switching contacts in an above described switching device according to the present invention. Such switching devices are, in particular, low-voltage switching devices such as contactors, power circuit-breakers, motor protection switches, feeder circuit-breakers, or the like.

According to the method, the structure-borne sound signals produced by the switching operation in the contact pieces 4d are captured, the captured structure-borne sound signals are subjected to a Fourier transform in discrete time windows to produce a sonogram, individual function values are selectively determined from the sonogram and evaluated using an evaluation device, a remaining service life being assigned and made available for output and/or display. FIG. 3 shows sonogram in a schematic representation. Time characteristics of the signal energy are determined from the sonogram over the entire frequency width and/or in one or a plurality of frequency bands M or single frequencies, respectively. Preferred function values for the feature formation include the peak value of at least one sonogram amplitude, the rise time of a sonogram amplitude from the occurrence of the signal to its maximum value, the decay time of the sonogram amplitude from its maximum value to a defined end value as well as the centroid of the amplitude area or of the amplitude space of a sonogram image. The area centroid or spatial centroid is determined by the point at which, on average, the highest signal intensity is located. In this context, it is possible to image signal characteristics in a time interval (three-dimensional image) or at a point in time (two-dimensional image). For feature formation, moreover, it is possible to cross-correlate the current sonogram (from the measured actual values) with the characteristics of a least one corresponding reference sonogram.

The structure-borne sound signals are captured by an above described structure-borne sound sensor 8, in particular, a piezoelectric element.

In a first possible embodiment, at least one frequency band (frequency range or a single frequency) is selected from the captured sound signals. In this manner, interference effects are eliminated and only the information which is characteristic of the "monitored" contact piece 4d are filtered out. Then, the signals of the entire frequency band are integrated and the generated integrated value is evaluated using an evaluation unit. This is carried out, for example, with the aid of a microprocessor, reference data for unused and/or used up contact pieces 4d being stored in the microprocessor. It is thus possible to compare the determined integrated value to the corresponding reference value, and to determine the expected remaining service life as a function of the occurring deviation (actual value/set point value). The reference values can be stored in the evaluation unit in the form of known or measured empirical values prior to the initial operation. In an alternative embodiment, the reference values can also be simply read in and stored when the new switching device is put into operation for the first time.

If only one frequency band is evaluated, it is preferred here to evaluate a frequency band having a bandwidth of 20 kHz to 225 kHz or even up to 500 kHz.

In a second embodiment of the present invention, the captured structure-borne sound signals are evaluated in at least two, preferably three different frequency bands. In this context, analogously to the first embodiment, the time integral of the occurring sonogram amplitudes is formed in each individual frequency band, and the values obtained in this manner are compared to corresponding reference values and evaluated.

In a further embodiment of the method, analogously to the second embodiment, three different frequency bands are selected but compressed only in two of them by generating the integrated values accordingly. In one of the frequency bands, only the amplitude value of the sonographic characteristic is determined. Thus, for one evaluation, two integrated values and one sonogram amplitude value are further processed and evaluated.

Figure 4:
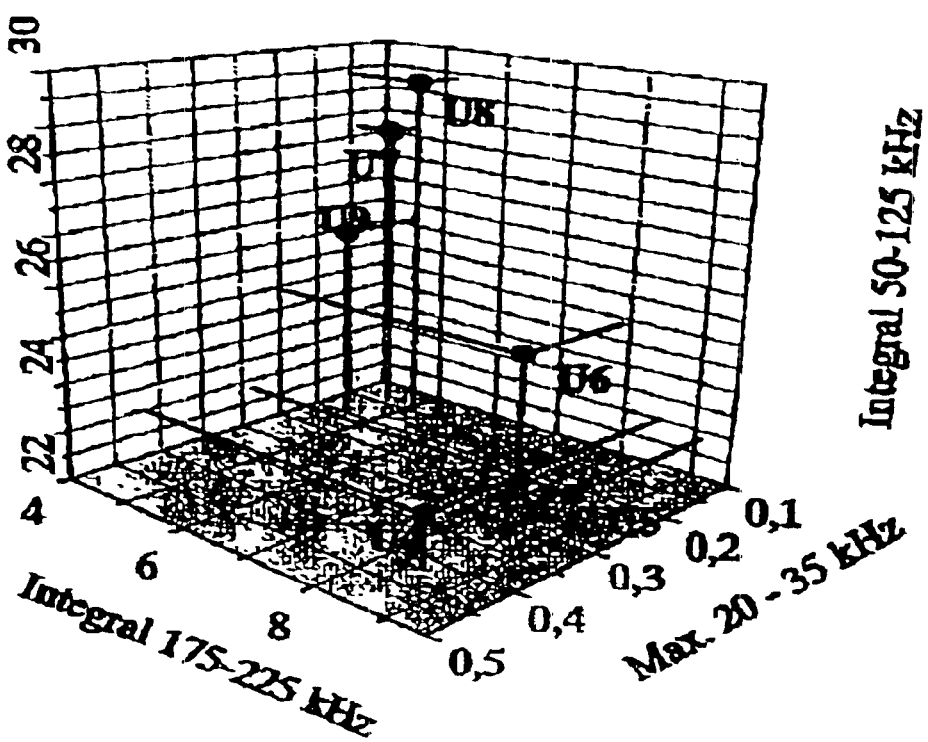
FIG. 4 depicts the determined features or feature spaces in a three-dimensional frequency space.

The preferred frequency band ranges are 20 kHz–35 kHz, 50 kHz–125 kHz and 150 kHz–225 kHz. In this context, in the latter-described embodiment of the method, the amplitude value of the sonographic signal characteristic is preferably determined in the frequency range between 20 kHz and 35 kHz. This amplitude value is preferably determined in a time interval of three to six milliseconds after the closing of the switching contacts 4a, 4b. FIG. 4 shows a possibility of imaging features for the described method, corresponding feature spaces being imaged through the previously determined values (two integrated values of the sonogram and an amplitude value of the sonogram). In the representation shown, the feature spaces formed by feature points U4, U5 and U6 indicate worn contact pieces 4d, and the feature spaces formed by feature points U7, U8 and U9 are a sign of contact pieces which are nearly free of wear.

The present invention is not limited to the specific embodiments described above but includes also all equally acting embodiments along the lines of the present invention. In a further embodiment, it is also possible for a sound sensor to be so designed as to ensure a defined production and injection of sound. This allows a switching device to be examined, preferably while it is de-energized, for its expected remaining service life, in that contact piece 4d to be examined is excited in a defined manner (injection of a known sound spectrum) via sound sensor 8 while the change in the injected sound waves due to a specific quality of contact piece 4d to be examined is captured nearly simultaneously and can be evaluated. To this end, it is preferred to use at least two, in particular, four separate sound sensors 8 or one sound sensor 8 having independent capturing regions. In this manner, it is possible for individual local areas of a contact piece 4d to be captured and evaluated separately. In a further refinement, the different sound sensors 8 can be assigned different weightings. This can be accomplished via a different evaluation in the microprocessor or else, by sound sensors 8 having different sensitivity.

What is claimed is:

1. A method for determining a remaining service life of switching contacts in an electrical switching device, the method comprising:

operating the switching contacts so as to produce structure-borne sound signals;

capturing the structure-borne sound signals;

performing a Fourier transform on the structure-borne sound signals in a plurality of discrete time windows so as to produce a sonogram;

determining a plurality of function values using the sonogram; and evaluating the plurality of function values using an evaluation device.

2. The method as recited in claim 1 wherein the electrical switching device is a low-voltage switching device.

3. The method as recited in claim 2 wherein the determining of the plurality of function values is performed within a single frequency band of the sonogram.

4. The method as recited in claim 3 wherein the determining of the plurality of function values is performed at a single frequency of the sonogram.

5. The method as recited in claim 3 wherein the frequency band includes a bandwidth of 20 kHz to 225 kHz.

6. The method as recited in claim 1 wherein the determining of the plurality of function values is performed within a plurality of frequency bands.

7. The method as recited in claim 6 wherein the plurality of frequency bands includes a first frequency band having a bandwidth of 20 kHz to 35 kHz, a second frequency band having a bandwidth of 50 kHz to 125 kHz, and a third frequency band having a bandwidth of 175 kHz to 225 kHz.

8. The method as recited in claim 1 wherein the determining of the plurality of function values is performed at a plurality of discreet frequencies.

9. The method as recited in claim 1 wherein the plurality of function values includes a peak amplitude value of a sonogram.

10. The method as recited in claim 1 wherein the plurality of function values includes a rise time of an amplitude of the sonogram.

11. The method as recited in claim 1 wherein the plurality of function values includes a decay time of an amplitude of the sonogram.

12. The method as recited in claim 1 wherein the plurality of function values includes at least one of an area centroid and a spatial centroid of the sonogram.

13. The method as recited in claim 1 wherein the determining of the plurality function values includes calculating a time integral of an amplitude of the sonogram in at least one frequency band.

14. The method as recited in claim 1 wherein the evaluating of the function value includes comparing the function value to a reference value.

15. The method as recited in claim 1 wherein the operating of the switching contacts includes at least one of opening and closing the switching contacts and wherein the structure-borne sound signals include sound signals produced during at least one of an opening or closing operation.

16. An electrical switching device comprising:
 a first switching contact;
 a second switching contact in an operable relationship to the first switching contact;
 a first sound sensor configured to capture first structure-borne sound signals produced by an operation of the first and second switching contacts; and
 an evaluation device configured to evaluate the first structure-borne signals so as to determine a remaining service life of at least one of the first and second switching contacts.

17. The electrical switching device as recited in claim 16 wherein the first sound sensor is associated with at least one of the first and second contact.

18. The electrical switching device as recited in claim 16 wherein the first sound sensor includes a piezoelectric element.

19. The electrical switching device as recited in claim 16 wherein the first sound sensor is further configured to produce a defined sound for injecting into the first switching contact.

20. The electrical switching device as recited in claim 16 further comprising a second sound sensor configured to capture second structure-borne sound signals and wherein the first structure-borne sound signals are associated with a first portion of the first switching contact and the second structure-borne sound signals are associated with a second portion of the first switching contact.

21. The electrical switching device as recited in claim 20 wherein the evaluation device is further configured to evaluate the second structure-borne signals, the evaluation device assigning a different weight to the first and second structure-borne sound signals.

22. The electrical switching device as recited in claim 20 wherein the first sound sensor has a first sound capture sensitivity and the second sound sensor has a second sound capture sensitivity.

23. The electrical switching device as recited in claim 20 further comprising a third sound sensor configured to capture third structure-borne sound signals and a fourth sound sensor configured to capture fourth structure-borne sound signals, and wherein each of the first, second, third, and fourth structure-borne sound signals are associated with a respective quarter of the first switching contact.

24. The electrical switching device as recited in claim 1 further comprising a contact carrier and wherein the first switching contact is mounted to a first side of the contact carrier and the first sound sensor is disposed on a second side of the contact carrier opposite the first switching contact.

25. The electrical switching device as recited in claim 24 wherein the first sound sensor is galvanically separated from the contact carrier.

26. The electrical switching device as recited in claim 24 wherein a ceramic sound sensor carrier is disposed between the sound sensor and the contact carrier.

27. The electrical switching device as recited in claim 16 wherein the first sound sensor is configured to capture sound signals having frequencies of 20 kHz–225 kHz.

28. The electrical switching device as recited in claim 16 wherein the first sound sensor is configured to capture sound signals having frequencies of 20 kHz–500 kHz.

29. The electrical switching device as recited in claim 16 wherein the evaluation device is disposed near to the other components of the electrical switching device.

30. The electrical switching device as recited in claim 16 wherein the evaluation device is disposed remote from the other components if the electrical switching device.

* * * * *